United States Patent [19]

Podraza

[11] Patent Number: 5,114,493
[45] Date of Patent: May 19, 1992

[54] SMOKING COMPOSITIONS CONTAINING A HEXAHYDROBENZOFURANONE FLAVORANT

[75] Inventor: Kenneth F. Podraza, Richmond, Va.

[73] Assignees: Philip Morris Inc., New York, N.Y.; Philip Morris Products Inc., Richmond, Va.

[21] Appl. No.: 266,161

[22] Filed: Nov. 2, 1988

[51] Int. Cl.$^5$ .............. A24B 3/12; C07D 307/02; C07D 407/00; C07D 305/12
[52] U.S. Cl. .................. 131/276; 131/277; 131/275; 549/323; 549/295
[58] Field of Search .............. 131/276, 277, 275; 549/323, 295

Primary Examiner—V. Millin
Attorney, Agent, or Firm—Arthur I. Palmer, Jr.; James E. Schardt; George A. Depaoli

[57] ABSTRACT

This invention provides smoking compositions which contains a 6-substituted hexahydrobenzofuranone flavorant additive.

Under cigarette smoking conditions the flavorant additive enhances the aroma and flavor of the cigarette smoke.

16 Claims, No Drawings

SMOKING COMPOSITIONS CONTAINING A HEXAHYDROBENZOFURANONE FLAVORANT

BACKGROUND OF THE INVENTION

The utilization of lactone compounds as flavorants in tobacco products has been proposed. Various lactones are known to contribute desirable properties to the flavor and aroma of tobacco products under smoking conditions.

U.S. Pat. No. 3,251,366 describes tobacco products that contain a lactone flavorant additive such as $\alpha,\beta$-dimethyl-$\gamma$-pentyl-hydroxybutenolide which imparts a celery-like note to mainstream smoke.

U.S. Pat. No. 3,372,699 and U.S. Pat. No.3,372,700 describe the use of a lactone such as $\beta$-methylbutyrolactone or 4-hydroxy-4-methyl-5-hexenoic acid $\gamma$ lactone as a flavorant additive in tobacco products.

U.S. Pat. No. 3,380,457; U.S. Pat. No. 3,563,248; and U.S. Pat. No. 3,861,403 describe other lactones which are recommended for use as flavorant additives in tobacco products, such as $\beta$-methyl-$\delta$-valerolactone, 3-(2-hydroxycyclohexyl)propionic acid $\delta$ lactone, 4-methyl-6-n-pentyl-$\alpha$-pyrone, and the like.

U.S. Pat. No. 4,407,740 describes disubstituted di- and tetra-hydrofuranones for utility in scenting or flavoring agents for imparting a coconut note.

U.S. Pat. No. 4,690,157 describes lactone flavorant-release additives for smoking compositions, such as 2-(1-hydroxy-1-phenylmethyl)-$\gamma$-butyrolactone.

Of particular interest with respect to the present invention are literature references which disclose 6-substituted hexahydrobenzofuranone derivatives. Chemical Abstracts lists compounds such as 6-methylhexahydro-2(3H)-benzofuranone [RN 22532-23-6]; 6-tertiary-butylhexahydro-2(3H)-benzofuranone [RN 54281-03-7]; and 6-(2-methyl-1,3-dioxolan-2-yl)hexahydro-2(3H)-benzofuranone [RN 65441-27-2].

There is continuing research effort to develop improved smoking compositions which generate mainstream smoke with flavorant-enhanced taste and character under smoking conditions.

Accordingly, it is an object of this invention to provide smoking compositions having incorporated therein a flavorant component which is characterized by lack of an undesirable mobility and/or volatility at ambient temperature.

It is another object of this invention to provide smoking compositions having incorporated therein a flavorant additive which under normal smoking conditions imparts improved flavor to mainstream smoke and improved aroma to sidestream smoke.

It is a further object of this invention to provide novel 6-substituted hexahydrobenzofuranone compounds which are adapted to be incorporated into cigarette fillers, and which under normal smoking conditions enhance the flavor and aroma of cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001-5 weight percent, based on the total weight of filler, of a hexahydrobenzofuranone flavorant additive corresponding to the formula:

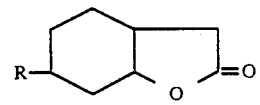

where R is a $C_1$-$C_6$ alkyl, $C_1$-$C_4$ alkylphenyl or $C_1$-$C_4$ alkoxyphenyl substituent.

Illustrative of substituents corresponding to R in the above represented formula are $C_1$-$C_6$ alkyl, $C_1$-$C_4$ alkylphenyl and $C_1$-$C_4$ alkoxyphenyl radicals such as methyl, ethyl, propyl, isopropyl, butyl, isobutyl, tertiary-butyl, 2-butyl, pentyl, hexyl, isohexyl, 4-methylphenyl, 2,4-dimethylphenyl, 4-propylphenyl, 4-butylphenyl, 4-methoxyphenyl, 4-ethoxyphenyl, 3-butoxyphenyl, and the like.

Diastereomeric mixtures of the 6-substituted hexahydrobenzofuranones can be separated by techniques such as high pressure liquid chromatography to provide separate cis and trans isomer fractions with a purity of at least about 90 percent by weight.

Preparation Of 6-Substituted Hexahydrobenzofuranones

A general procedure for preparation of 6-substituted hexahydrobenzofuranones involves (1) the reaction of a 3-substituted 2-cyclohexen-1-one with a strong base to form an organometallic carbanion at the 6-position of the cyclohexenone; (2) the coupling of the carbanion position with 2-haloacetate; (3) the reduction of the $\alpha,\beta$-unsaturated ketone functionality to a 1hydroxy structure; and (4) cyclization under acidic conditions to form the desired 6-substituted hexahydrobenzofuranone.

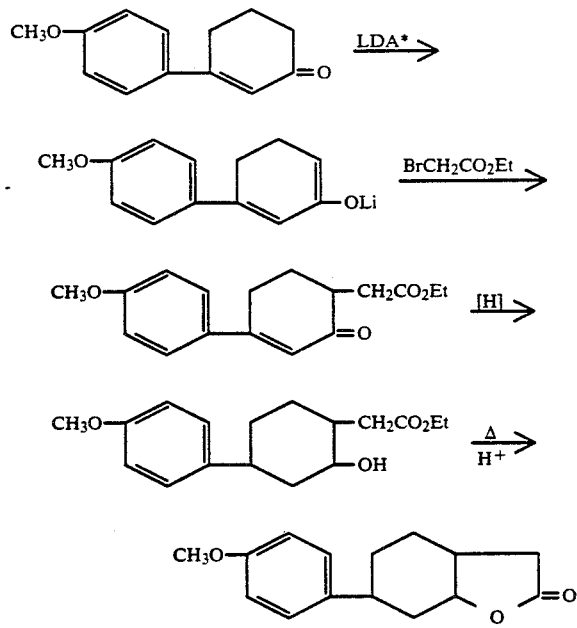

*Lithium diisopropylamide

Preparation Of Tobacco Compositions

In a further embodiment, the present invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant additive corresponding to the formula:

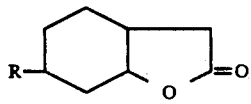

where R is a $C_1$-$C_6$ alkyl, $C_1$-$C_4$ alkylphenyl or $C_1$-$C_4$ alkoxyphenyl substituent.

The invention flavorant additive can be incorporated into the tobacco or tobacco substitute in accordance with methods known and used in the art. Preferably the flavorant additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5-5 weight percent, based on the weight of filler, and then subsequently to blend the treated filler with filler which does not contain flavorant additive.

The term "tobacco substitute" is meant to include non-tobacco smoking filler materials such as are disclosed in United States Pat. Nos. 3,703,177; 3,796,222; 4,019,521; 4,079,742; and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°-750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

EXAMPLE I

This Example illustrates the preparation of cis and trans hexahydro-2(3H)-benzofuranone.

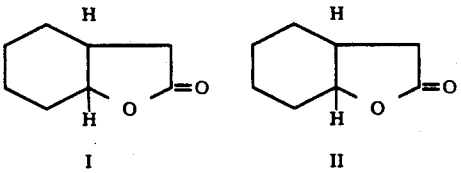

To a solution of 1.0 g (5.43 mmoles) of ethyl 2-cyclohexanoneacetate in 10 ml of tetrahydrofuran (THF) was added 0.34 g (5.43 mmoles) of sodium cyanoborohydride at room temperature. The mixture was acidified to a pH of approximately 2 with a solution of hydrochloric acid in tetrahydrofuran (1:4 concentrated hydrochloric acid in THF). The solution was stirred for 2 hours at room temperature under a nitrogen atmosphere, then refluxed for 44 hours. The mixture was allowed to cool to room temperature, followed by neutralization with aqueous saturated sodium bicarbonate.

The solution was extracted with ether, and the combined ether extracts were dried over anhydrous magnesium sulfate and evaporated under reduced pressure. The crude product residue was purified by semipreparative high pressure liquid chromatography utilizing a silica gel column with 20% ethyl acetate in hexane as the eluent. The first component eluted was the trans isomer (0.50 g) and the second component was the cis isomer (0.15 g) in an overall 76% yield.

NMR and IR data confirm the above structures.

EXAMPLE II

This Example illustrates the preparation of cis and trans 6-methylhexahydro-2(3H)-benzofuranone.

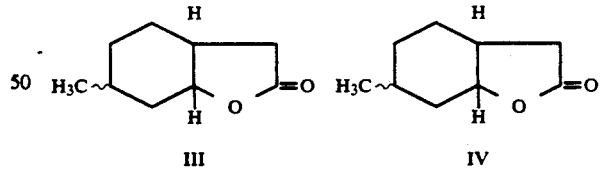

A solution of 10.08 g (99.8 mmoles) of diisopropylamine in 150 ml of THF under argon and at −78° C. was prepared, and 39.9 ml (99.8 mmoles) of 2.5 M of n-butyllithium in hexane were rapidly added to the solution. The resultant reaction mixture was stirred for about 5 minutes, followed by the rapid addition of 10.0 g (90.7 mmoles) of 3-methyl-2-cyclohexen-1-one in 30 ml of THF while maintaining the reaction mixture temperature below −50° C. The solution was stirred for 15 minutes, then 18.18 g (108.8 mmoles) of ethyl bromoacetate in 30 ml of THF were added, while maintaining a temperature below −50° C.

The solution was stirred for one hour at −78° C., then diluted with ether and quenched with saturated NH₄Cl. The mixture was warmed to approximately 0° C., and the aqueous layer was extracted with ether. The combined organic extracts were washed with aqueous saturated NH₄Cl and with aqueous saturated NaCl, then dried over anhydrous MgSO₄ and evaporated under reduced pressure. The material was purified by Kugelrohr distillation (bp 72°-90° C./0.01 mm Hg) to yield 14.31 g (80%) of 6-(carbethoxymethyl)-3-methyl-2-cyclohexen-1-one.

6-(Carbethoxymethyl)-3-methyl-2-cyclohexen-1-one (3.0 g) was added to a mixture of 0.25 g of platinum oxide in 100 ml of 95% ethanol and 90 mg of sodium nitrite. This mixture was hydrogenated under a hydrogen atmosphere (maximum pressure 45 psi) for 17.5 hours. The mixture was filtered and the solvent was removed under reduced pressure.

The resulting oil was mixed with 100 ml of glacial acetic acid and was refluxed (oil bath temperature 120°) for 2 hours. The solution was cooled to room temperature and the solvent was removed under reduced pressure. The crude oil residue was purified by Kugelrohr distillation (bp 50°-60° C./0.01 mm Hg) to yield 2.0 g (86%) of 6-methylhexahydro-2(3H)-benzofuranone as a mixture of diastereomers.

The diastereomeric mixture was subjected to high pressure liquid chromatography utilizing a silica gel column and 10% ethyl acetate in hexane as the eluent. The trans isomer eluted before the cis isomer during the separation procedure.

NMR and IR data confirm the above structures.

EXAMPLE III

This Example illustrates the preparation of a 6-n-butylhexahydro-2(3H)-benzofuranone diastereomeric mixture.

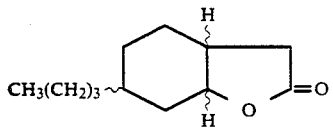

The reaction of 3-n-butyl-2-cyclohexen-1-one (3.0 g, 19.7 mmoles) in 10 ml of THF with lithium diisopropylamide (2.17 mmoles) followed by ethyl bromoacetate (3.96 g, 23.6 mmoles) in 10 ml of THF, at −78° C. under argon, was conducted in a similar manner to the synthesis of 6-(carbethoxymethyl)-3-methyl-2-cyclohexen-1-one described in Example II, and a yield of 3.92 g (83%) of 6-(carbethoxymethyl)-3-n-butyl-2-cyclohexen-1-one was obtained.

The reduction of 6-(carbethoxymethyl)-3-n-butyl-2-cyclohexen-1-one (2.0 g) in 50 ml of glacial acetic acid with 0.5 g of platinum oxide was performed in accordance with the procedure of Example II.

The recovered oil product (2.0 g) was mixed with 10 ml of 10% HCl, and the resulting emulsion was heated at 80° C. for 1.5 hours. The product mixture was cooled to room temperature and extracted with ether. The combined ether extracts were washed with H₂O and with aqueous saturated sodium bicarbonate, then dried over anhydrous MgSO₄ and evaporated under reduced pressure. The crude oil product was purified by high pressure liquid chromatography utilizing a silica gel column and 15% ethyl acetate in hexane as the eluent. A yield of 0.82 g (50%) of 6-n-butylhexahydro-2(3H)-benzofuranone was obtained as a mixture of diastereomers.

NMR and IR confirm the above structure. Anal. Calc. for C₁₂H₂₀O₂: C,73.43; H,10.27. Found: C,73.20; H,10.05

EXAMPLE IV

This Example illustrates the preparation of a 6-phenylhexahydro-2(3H)-benzofuranone diastereomeric mixture.

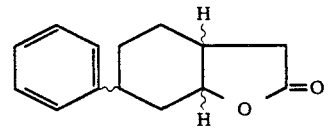

The reaction of 3-phenyl-2-cyclohexen-1-one (3.0 g, 17.4 mmoles) in 10 ml of THF with lithium diisopropylamide (19.2 mmoles) followed by ethyl bromoacetate (3.5 g, 20.9 mmoles) in 10 ml of THF, at −78° C. under argon, was conducted in a similar manner to the synthesis of 6-(carbethoxymethyl)-3-methyl-2-cyclohexen-1-one described in Example II. A yield of 3.90 g (87%) of 6-(carbethoxymethyl)-3-phenyl-2-cyclohexen-1-one was obtained.

6-(Carbethoxymethyl)-3-phenyl-2-cyclohexen-1-one (2.11 g) was added to a mixture of 0.2 g of 10% palladium on carbon in 30 ml of ethyl acetate. The reaction mixture was hydrogenated under a hydrogen atmosphere (maximum pressure 45 psi) for 41 hours. The mixture was filtered through celite, and the solvent was removed under reduced pressure. The recovered crude oil product was purified by chromatography on silica gel eluted with 5% ethyl acetate in hexane to provide 1.5 g (71%) of 6-(carbethoxymethyl)-3-phenylcyclohexanone.

To a mixture of 1.47 g of lithium tri-tert-butoxyaluminohydride in anhydrous ether at room temperature was added 1.0 g of 6-(carbethoxymethyl)-3-phenylcyclohexanone in 5 ml of anhydrous ether, and the reaction mixture was stirred for 4 hours at room temperature. Water was added to the mixture, and the organic layer was separated and washed with aqueous saturated ammonium chloride, then dried over anhydrous MgSO₄ and evaporated under reduced pressure.

The resulting oil product (1.0 g) was mixed with 20 ml of dry tetrahydrofuran, and the solution was acidified to a pH of approximately 1 utilizing concentrated hydrochloric acid. The solution was refluxed for 16 hours, and then allowed to cool to room temperature. Ether was added and the solution was neutralized with aqueous saturated sodium bicarbonate. The organic layer was separated, dried over anhydrous MgSO₄, and evaporated under reduced pressure. The semi-solid crude material was purified by high pressure liquid chromatography utilizing a silica gel column with 15% ethyl acetate in hexane as the eluent to yield 372 mg (45%) of 6-phenylhexahydro-2(3H)-benzofuranone as a mixture of diastereomers.

NMR and IR data confirm the above structure.
Anal. Calc. for C₁₄H₁₆O₂: C,77.75; H,7.46. Found: C,77.94; H,7.42.

The same synthesis procedures are followed for the production of 6-(4-methoxyphenyl)hexahydro-2(3H)-benzofuranone and 6-(4-ethylphenyl)hexahydro-2(3H)-benzofuranone, respectively.

EXAMPLE V

This Example illustrates the subjective evaluation of the aroma properties of the Examples I–IV products by a panel of experts.

The description of the aroma properties are as follows:

| Compound | Aroma Properties |
| --- | --- |
| I. cis hexahydro-2(3H)-benzofuranone | almond, coconut, sweet and spicy odor. |
| II. trans hexahydro-2(3H)-benzofuranone | higher level of almond and sweet odor than cis derivative. |
| III. cis 6-methylhexahydro-2(3H)-benzofuranone | almond, coconut, sweet and spicy odor. |
| IV. trans 6-methylhexahydro-2(3H)-benzofuranone | higher level of almond and sweet odor than cis derivative. |
| V. 6-n-butylhexahydro-2(3H)-benzofuranone | fruity, sweet, fatty and green odor. |
| VI. 6-phenylhexahydro-2(3H)-benzofuranone | essentially no odor at room temperature. |

In general, products III and IV had a more intense response rating by the panel evaluators as compared to products I and II.

EXAMPLE VI

This Example illustrates the preparation of smoking compositions in accordance with the present invention, and subjective evaluation of the compositions by an experienced smoking panel.

Cigarettes were fabricated employing a blend of tobaccos treated with an ethanolic solution of the test flavorant. The cigarettes were targeted to deliver 8 mg of tar per cigarette. Untreated controls were prepared, and the treated cigarettes were compared to the controls.

An isomeric mixture of cis and trans hexahydro-2(3H)-benzofuranone (Example I) exhibited a sweet vanilla-like flavor as compared to the control, at 0.005% by weight.

An isomeric mixture of cis and trans 6-methylhexahydro-2(3H)-benzofuranones (Example II) was found to impart a sweet, coconut and smoother flavor as compared to the control, at 0.0001% by weight. At a 0.002% by weight content of flavorant in the tobacco filler, the treated cigarettes were described as exhibiting a sweet, powdery, spicy and toasted flavor as compared to the controls.

A mixture of 6-n-butylhexahydro-2(3H)-benzofuranone isomers (Example III) exhibited a waxy, floral flavor as compared to the control, at 0.005% by weight.

A mixture of 6-phenylhexahydro-2(3H)-benzofuranone isomers (Example IV) exhibited a dusty sweet flavor as compared to the control, at 0.02% by weight.

What is claimed is:

1. A smoking composition comprising an admixture of (1) combustible filler selected from natural tobacco, reconstituted tobacco and tobacco substitutes, and (2) between about 0.0001–5 weight percent, based on the total weight of filler, of a hexahydrobenzofuranone flavorant additive corresponding to the formula:

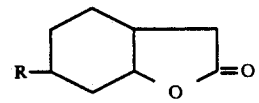

where R is a $C_1$–$C_6$ alkyl, $C_1$–$C_4$ alkylphenyl or $C_1$–$C_4$ alkoxyphenyl substituent.

2. A smoking composition in accordance with claim 1 wherein the flavorant additive is 6-methylhexahydro-2(3H)-benzofuranone.

3. A smoking composition in accordance with claim 1 wherein the flavorant additive is cis 6-methylhexahydro-2(3H)-benzofuranone with a purity of at least about 90 percent by weight.

4. A smoking composition in accordance with claim 1 wherein the flavorant additive is trans 6-methylhexahydro-2(3H)-benzofuranone with a purity of at least about 90 percent by weight.

5. A smoking composition in accordance with claim 1 wherein the flavorant additive is 6-n-butylhexahydro-2(3H)-benzofuranone.

6. A smoking composition in accordance with claim 1 wherein the flavorant additive is 6-phenylhexahydro-2(3H)-benzofuranone.

7. A smoking composition in accordance with claim 1 wherein the flavorant additive is 6-(4-methoxyphenyl)-hexahydro-2(3H)-benzofuranone.

8. A smoking composition in accordance with claim 1 wherein the flavorant additive is 6-(4-ethylphenyl)hexahydro-2(3H)-benzofuranone.

9. A method of preparing a smoking composition which is adapted to impart flavor and aroma to mainstream and sidestream smoke under smoking conditions, which method comprises incorporating into natural tobacco, reconstituted tobacco or tobacco substitute between about 0.0001–5 weight percent, based on composition weight, of a hexahydrobenzofuranone flavorant additive corresponding to the formula:

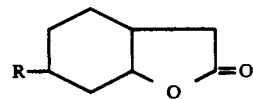

where R is a $C_1$–$C_6$ alkyl, $C_1$–$C_4$ alkylphenyl or $C_1$–$C_4$ alkoxyphenyl substituent.

10. cis 6-Methylhexahydro-2(3H)-benzofuranone.

11. trans 6-Methylhexahydro-2(3H)-benzofuranone with a purity of at least about 90 percent by weight.

12. 6-n-Butylhexahydro-2(3H)-benzofuranone.

13. 6-Phenylhexahydro-2(3H)-benzofuranone.

14. 6-(4-Methoxyphenyl)hexahydro-2(3H)-benzofuranone.

15. 6-(4-Ethylphenyl)hexahydro-2(3H)-benzofuranone.

16. A diastereometric mixture of cis 6-methylhexahydro-2-(3H)-benzofuranone and trans 6-methylhexahydro-2(3H)-benzofuranone.

* * * * *